(12) United States Patent
Metcalfe

(10) Patent No.: US 7,429,112 B2
(45) Date of Patent: Sep. 30, 2008

(54) RETRO-REFLECTOR ASSEMBLY AND OPACITY MONITOR INCORPORATING SAME

(75) Inventor: Stuart Francis Metcalfe, Sheffield (GB)

(73) Assignee: Land Instruments International Ltd. (GB)

( * ) Notice: Subject to any disclaimer, the term of this patent is extended or adjusted under 35 U.S.C. 154(b) by 20 days.

(21) Appl. No.: 11/429,773

(22) Filed: May 8, 2006

(65) Prior Publication Data

US 2006/0285116 A1    Dec. 21, 2006

(30) Foreign Application Priority Data

Jun. 16, 2005    (GB) ................... 0512261.9

(51) Int. Cl.
*G02B 5/122* (2006.01)
(52) U.S. Cl. ...................... 359/529; 359/834
(58) Field of Classification Search ............... 359/529, 359/831–838, 530
See application file for complete search history.

(56) References Cited

U.S. PATENT DOCUMENTS 4,470,664 A * 9/1984 Shirasawa ................... 359/529
5,231,539 A   7/1993 McMillen
5,893,214 A * 4/1999 Meier et al. ................. 33/293
6,781,695 B2  8/2004 Hovan et al.
2003/0038940 A1  2/2003 Metcalfe et al.
2004/0169928 A1  9/2004 Nilsen et al.

FOREIGN PATENT DOCUMENTS

JP    60-225102    11/1985

OTHER PUBLICATIONS

Extended European Search Report dated Oct. 2, 2006 which issued in connection with corresponding European Application No. 06076032.9.

* cited by examiner

*Primary Examiner*—Euncha P Cherry
(74) *Attorney, Agent, or Firm*—Trexler, Bushnell, Giangiorgi, Blackstone & Marr, Ltd.

(57) ABSTRACT

A retro-reflector assembly (1) for incorporating in an opacity monitor, includes several small corner-cube prisms (2) of cylindrical section. The invention also includes an opacity monitor incorporating a retro-reflector assembly as defined above.

10 Claims, 1 Drawing Sheet

RETRO-REFLECTOR ASSEMBLY AND OPACITY MONITOR INCORPORATING SAME

RELATED/PRIORITY APPLICATION

This application claims the benefit of British application Ser. No. 0512261.9, filed Jun. 16, 2005.

FIELD OF THE INVENTION

This invention relates to a retro-reflector assembly and to an opacity monitor incorporating such a retro-reflector assembly for use in the monitoring of dust density within industrial chimney stacks, flues, ducts etc (hereinafter all generally referred to as "stacks").

BACKGROUND OF THE INVENTION

Many industrial processes emit dust from stacks. An example is coal-fired power stations. There is often a statutory requirement to continuously monitor the amount of dust being emitted.

A favoured technique is opacity monitoring. Here a light beam is projected across the stack and its attenuation measured. This measurement is correlated to the dust density in the stack.

Practical opacity monitors use an arrangement in which both the light source and detection are located at one side of the stack and a reflector at the other side. The advantage of using a retro-reflector assembly is based on the well-known property of a corner-cube prism to return a light beam exactly along its incident direction—irrespective of the precise orientation of the prism. This makes the system tolerant to misalignment of the retro-reflector assembly.

Opacity is derived from measurement of the projected and returned beam and is typically expressed as a percentage. If the returned beam power is say 70% of the projected beam power then the opacity is 30%.

However, opacity measurement becomes difficult in relatively clean, low-dust processes where the opacity is small—for example 5%. Consequently, if the measurement of either projected or returned beam power is subject to a drift of say 2 percent, then the error in the measured opacity also drifts 2 percent—ie two fifths of its true (5%) value.

Thus there is great interest in making opacity monitors with the highest possible stability. This stability must be maintained over time (many months) and temperature (a 40F. temperature cycle is a standard test stipulated by the USA Environmental Agency).

The most obvious sources of drift are in the light emission and detection assembly. This is a complex device often referred to a transmissometer and a good transmissometer will have a stability of about 2 percent.

However, very recent development work has resulted in transmissometer designs which are capable of stabilities of a few tenths of one percent. For example see U.S. Pat. No. 6,781,695.

However, a retro-reflector assembly is a simple, passive device but the efficiency with which it returns the incident light beam is, nevertheless, subject to variations with time and temperature. With the latest transmissometers, retro-reflector drift can become a significant component of the overall system drift.

OBJECT OF THE INVENTION

A basic object of the invention is the provision of an improved retro-reflector assembly and opacity monitor incorporating same which reflector/monitor has/have exceptional stability with both temperature-change and time.

Summary of a First Aspect of the Invention

According to the present invention, there is provided a retro-reflector assembly for use in an opacity monitor wherein the retro-reflector assembly includes a plurality of relatively small corner-cube prisms of cylindrical section.

Summary of a Second Aspect of the Invention

According to a second aspect of the invention, there is provided an opacity monitor incorporating a retro-reflector assembly in accordance with the first aspect.

Advantages of the Invention

The retro reflector assembly in accordance with the first aspect of the invention is exceptionally stable in relation to the proportion of incident light it returns, this stability being maintained over long periods of time and over large ambient temperature swings.

The retro-reflector assembly in accordance with the first aspect of the invention is very efficient in that it returns an unusually large proportion of the incident light beam, which assists system signal-to-noise ratio.

In addition, the retro-reflector assembly in accordance with the invention can be manufactured economically.

Furthermore, the retro-reflector assembly in accordance with the invention is easily adapted to include temperature control—to further enhance stability or to prevent condensation.

Preferred or Optional Features of the Invention

The prisms are made of glass.
The number of prisms is between 2 and 50.
The diameter of the prisms is between 3 mm and 20 mm.
The prisms are embedded in a metal substrate.
The metal substrate is an aluminum block.
Active faces of the prisms are sealed within a chamber inside the metal substrate.
The chamber is closed off by a cover with an 'O'-ring or similar sealing device.
The cover is secured to the metal substrate by screws.
The chamber contains a desiccant.
A heating element is embedded in the metal substrate.
The heating element comprises one or more resistors.
A temperature sensor is embedded in the metal substrate.
The temperature sensor is a thermocouple.
The heating element and/or temperature sensor are coupled to a conventional controller unit to hold the block at a pre-set temperature—eg above the 'dewpoint' at which water vapour might condense on the active faces of the prisms.
The retro-reflector assembly is mounted within an air-purge housing whose purpose is to prevent any atmospheric dirt from contaminating the active faces of the prisms.
The metal substrate is advantageously temperature-controlled by means of an embedded or otherwise attached heating element.

BRIEF DESCRIPTION OF THE DRAWINGS

The invention will now be further described, in greater detail, by way of example, with reference to the accompanying drawings, in which.

DESCRIPTION OF AN ILLUSTRATED EMBODIMENT OF THE INVENTION

Figure 1:
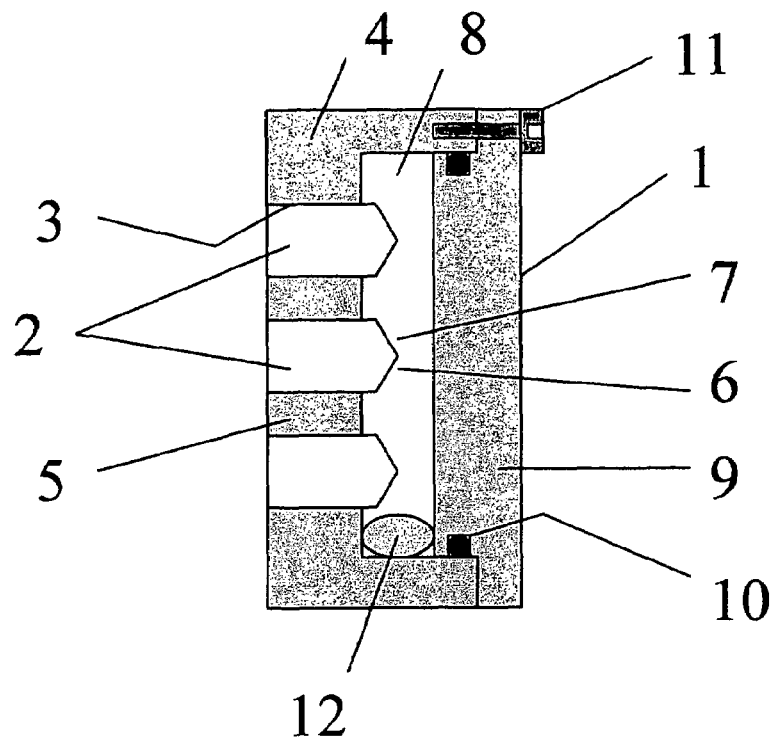
FIG. 1 is a schematic sectional view through a retro-reflector assembly in accordance with the first aspect of the invention.
Figure 2:
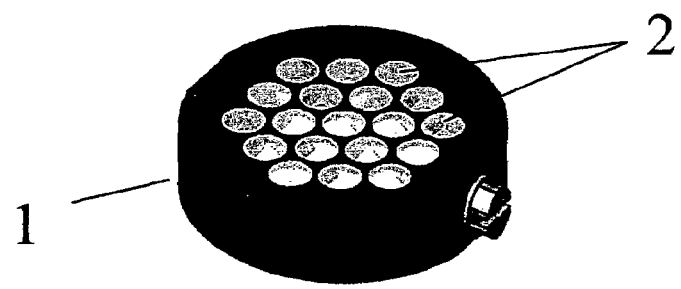
FIG. 2 is a front view of the reflector of FIG. 1.
Figure 3:
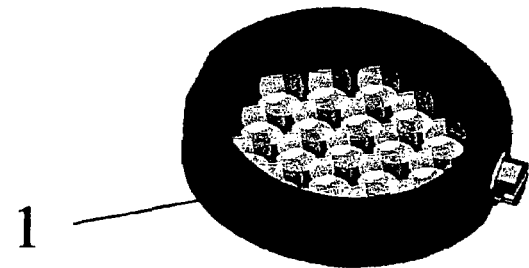
FIG. 3 is a rear view of the reflector of FIG. 1.

In the drawings, retro-reflector assembly 1 comprises a plurality of glass corner-cube prisms 2 bonded into holes 3 in an aluminum block 4. Separation lands 5 between prisms 2 are of a few millimeters dimension. Active faces 6 and 7 of each prism are sealed within a chamber 8 by closing a rear of the block 4 by a cover 9 with an 'O'-ring 10 or similar sealing mechanism. The cover is secured by screws 11 and moisture is removed using a small desiccant capsule 12.

The stability of an opacity monitor employing a retro-reflector assembly 1 as described above is quite exceptional. There is no measurable drift with time. The drift with temperature is typically 0.025% for a 40F. temperature change.

The efficiency of a retro-reflector assembly in accordance with the invention is also exceptional. The returned beam power is more than two times that obtained from a single glass retro-reflector assembly with diameter equal to the overall array diameter.

The invention claimed is:

1. A retro-reflector assembly for incorporation in an opacity monitor, said assembly comprising several corner-cube prisms each of which is of glass and each of which has a cylindrical external surface by which said prisms are embedded in closely spaced relationship in a metal substrate, which metal substrate either imparts, by its high thermal conductivity, compared with the thermal conductivity of said glass prisms, thermal stability to said assembly, and/or which metal substrate is thermally controlled to attain thermal stability.

2. A retro-reflector assembly as claimed in claim 1, wherein the number of prisms is between 2 and 50.

3. A retro-reflector assembly as claimed in claim 1, wherein said prisms each have a diameter between 3 mm and 20 mm.

4. A retro-reflector assembly as claimed in claim 1, wherein said metal substrate is an aluminium block.

5. A retro-reflector assembly as claimed in claim 1, wherein active faces of said prisms are sealed within a chamber inside said metal substrate.

6. A retro-reflector assembly as claimed in claim 5, wherein said chamber is closed off by a cover with an 'O'-ring or similar sealing device.

7. A retro-reflector assembly as claimed in claim 6, wherein said cover is secured to said metal substrate by screws.

8. A retro-reflector assembly as claimed in claim 5, wherein said chamber also contains a desiccant.

9. A retro-reflector assembly as claimed claim 1, wherein said metal substrate is temperature-controlled by means of an embedded, or otherwise attached, heating element.

10. An opacity monitor incorporating a retro-reflector assembly, said assembly comprising several corner-cube prisms each of which is of glass and each of which has a cylindrical external surface by which said prisms are embedded in closely spaced relationship in a metal substrate, which metal substrate either imparts, by its high thermal conductivity, compared with the thermal conductivity of said glass prisms, thermal stability to said assembly, and/or which metal substrate is thermally controlled to attain thermal stability.

* * * * *